United States Patent [19]

Ember

[11] Patent Number: 5,220,075
[45] Date of Patent: Jun. 15, 1993

[54] INITIATED PEROXIDATION OF SECONDARY CARBON IN ALKANES AND CYCLOALKANES

[75] Inventor: George Ember, Hackensack, N.J.

[73] Assignee: ABB Lummus Crest Inc., Bloomfield, N.J.

[21] Appl. No.: 915,897

[22] Filed: Jul. 17, 1992

[51] Int. Cl.$^5$ .................. C07C 409/02; C07C 409/14
[52] U.S. Cl. .................. 568/573; 568/568; 568/570; 568/571
[58] Field of Search ............ 568/568, 570, 571, 573

[56] References Cited

U.S. PATENT DOCUMENTS 3,987,115 10/1976 Zajacek et al. .................. 568/570
4,341,907 7/1982 Zelonka .......................... 568/573

FOREIGN PATENT DOCUMENTS 7709269 8/1977 Netherlands .................. 568/571

*Primary Examiner*—Werren B. Lone
*Attorney, Agent, or Firm*—Chilton, Alix & Van Kirk

[57] ABSTRACT

A secondary carbon atom in an alkane, including alkyl groups attached to aromatic rings, or cycloalkane is oxidized by molecular oxygen to the corresponding hydroperoxide in the absence of a catalyst. The oxidation is carried out in the presence of a tertiary hydroperoxide initiator which provides the free radicals needed to maintain the reaction. The amount of tertiary alcohol in the initiator is limited.

10 Claims, 1 Drawing Sheet

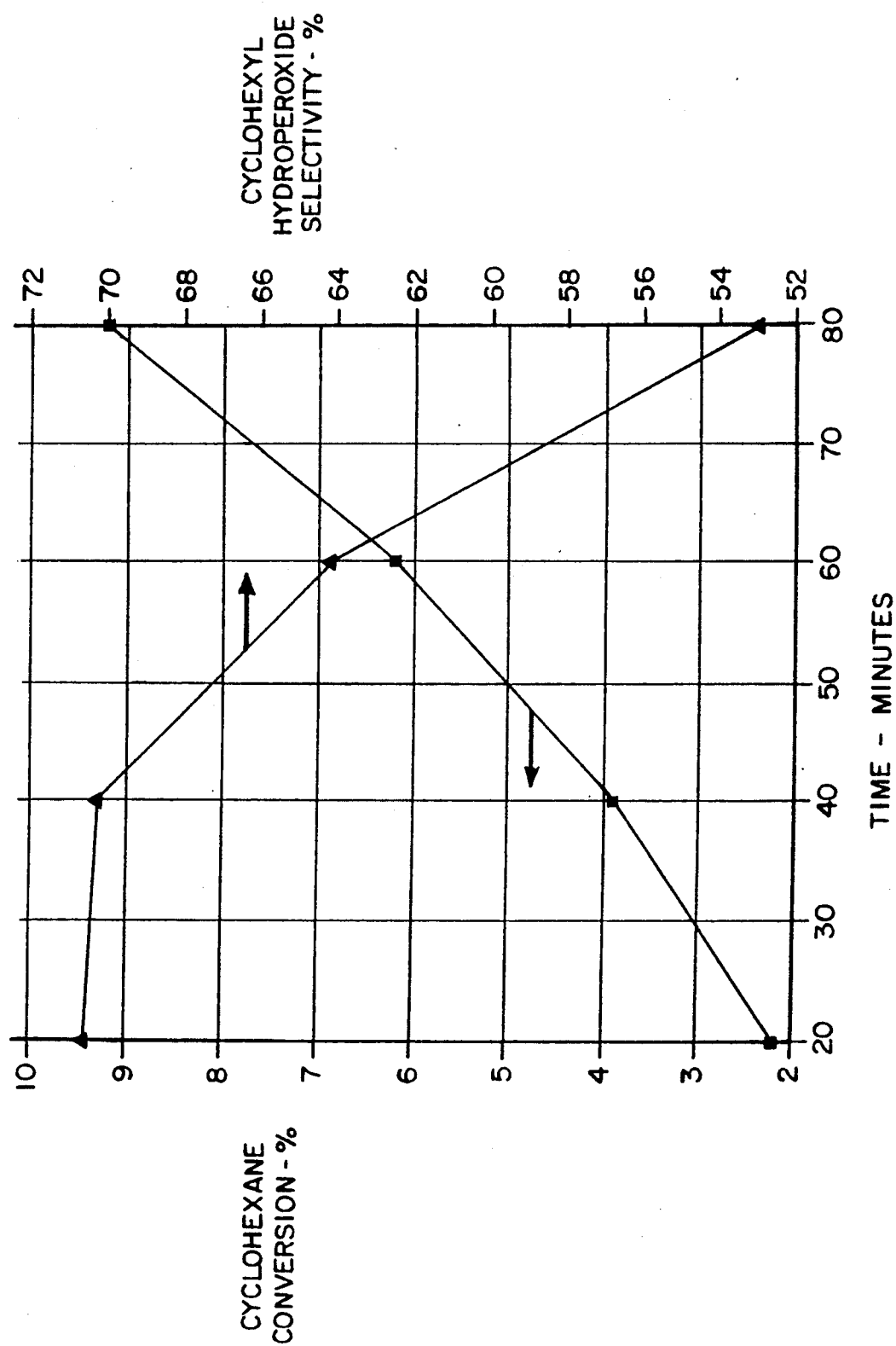

INITIATED PEROXIDATION OF SECONDARY CARBON IN ALKANES AND CYCLOALKANES

BACKGROUND OF THE INVENTION

The present invention relates to the peroxidation of secondary carbon in alkanes, including alkyl groups attached to aromatic rings and cycloalkanes.

It is well known that the various tertiary and secondary organic hydroperoxides are suitable as oxidants for a number of highly selective partial oxidations. Molecular oxygen is usually not very suitable for these oxidations since a selective or partial oxidation requires, in a storchrometric sense, the transfer of one oxygen atom only. For example, organic hydroperoxides are particularly effective for the synthesis of alcohols, aldehydes, ketones, epoxides, cyanates and oximes.

Typical industrial processes for oxidizing alkanes and cycloalkanes involve oxidation in the presence of a catalyst such as a cobalt-naphthanate catalyst. The peroxide which is formed is only transitory and is subject to decomposition in the presence of the catalyst. The primary products are the corresponding alcohol and ketone. For example, the most widely used oxidation process for cyclohexane has only about 4 to 5% conversion of the cyclohexane and the product is about 75% cyclohexanol and cyclohexanone with the remainder being various by-products. At higher conversion levels, the selectivity of products decreases because the cyclohexanone is readily oxidized to by-products. The solution is to minimize the formation of the cyclohexanone by keeping the conversion of cyclohexane at a low level or preventing the formation of cyclohexanone from cyclohexanol such as by esterification. None of these processes produce any significant quantity of the peroxide, cyclohexyl hydroperoxide, in the final product. Typically the amount is only 5 to 10% of the product.

The main objective of peroxidations is the production of the corresponding hydroperoxides. However, the decomposition of hydroperoxides is required to maintain the free radical type chain reaction. This represents a loss in selectivity for the desired hydroperoxide. In addition, the alcohols or ketones formed from the decomposition of secondary hydroperoxides are more readily oxidized than the corresponding hydrocarbons. This over-oxidation leads to the rupture of carbon-carbon bonds and to the formation of carboxylic acids, which also facilitate the decomposition of the hydroperoxides. The result is a rapid decrease in the selectivity of products with increasing conversion.

To avoid this yield loss, the oxidation/peroxidation of the secondary carbon in various alkanes and cycloalkanes has to be carried out without the usual transition metal ions, which catalyze the decomposition of hydroperoxides. Also, the reactions have to be stopped at relatively low conversion levels. The commercial use of secondary carbon oxidations is limited by these two problems. First, in a non-catalytic oxidation, the initiation of the chain reaction must rely on the thermal decomposition of some hydroperoxide. This means that at low temperature the reaction is very slow while at high temperature the selectivity is low. Secondly, to produce the hydroperoxide of the secondary carbon at high selectivity, one can not rely on its decomposition for supplying the free radicals.

U.S. Pat. No. 3,987,115 discloses a method for peroxidation with oxygen in the presence of a tertiary alcohol and a tertiary hydroperoxide. In this process, the minimum ratio of tertiary alcohol to the hydrocarbon is relatively high (0.05 to 1) and the minimum ratio of tertiary alcohol to tertiary hydroperoxide is also high (1.21 in Run 4 of Table 1) and it is stated that such a low level of tertiary alcohol is undesirable because of the drop in the yield. Although the tertiary alcohol, present in the reaction mixture will form esters with the acidic hydroperoxide and thereby stabilize the secondary hydroperoxide, the tertiary alcohol prevents the tertiary hydroperoxide from forming free radicals. This will reduce the rate and selectivity of the peroxidation reaction.

SUMMARY OF THE INVENTION

In accordance with the present invention, a secondary carbon atom in an alkane, including alkyl groups attached to aromatic rings, or cycloalkane hydrocarbon is oxidized by molecular oxygen to the corresponding hydroperoxide in the absence of a catalyst which would decompose the hydroperoxide. The oxidation is carried out in the presence of a tertiary hydroperoxide, which provides free radicals needed to maintain the reaction, with the content of tertiary alcohol being limited. The invention is particularly applicable to the peroxidation of cyclohexane to produce cyclohexyl hydroperoxide at a temperature of 100° C. to 200° C. and preferably 130° C. to 160° C. and a pressure of 700 to 1200 kPa using 0.5 to 5% and preferably 1 to 2% tertiary butyl hydroperoxide or tertiary amyl hydroperoxide. All percentages are expressed as mole percent unless otherwise noted.

It is an object of this invention to provide a method for the oxidation of the secondary carbon in alkanes and cycloalkanes to obtain a relatively high conversion and selectivity for the hydroperoxide.

BRIEF DESCRIPTION OF THE DRAWINGS

FIG. 1 is a graph of the cyclohexane conversion and the cyclohexyl hydroperoxide selectivity versus the reaction time for the present invention.

DESCRIPTION OF THE PREFERRED EMBODIMENTS

The present invention is applicable to the peroxidation of a variety of alkanes and cycloalkanes but will first be described with reference to peroxidation of cyclohexane to form cyclohexyl hydroperoxide.

The typical oxidation of cyclohexane relies on the catalytic decomposition of the cyclohexyl hydroperoxide which is decomposed to generate free radicals required to maintain the chain reaction. However, the decomposition of cyclohexyl hydroperoxide forms cyclohexanol and cyclohexanone. Therefore, the present invention minimizes the decomposition of cyclohexyl hydroperoxide by eliminating the catalyst and by decreasing the reaction temperature. Unless other steps were taken, this would result in a significant decrease in the reaction rate because of the drop in the concentration of free radicals available to carry out the reaction.

In order to regain a reaction rate comparable to the reaction rate of the catalytic process, the present invention adds a small amount (0.5 to 5% and preferably 1 to 2%) of a tertiary hydroperoxide such as tertiary butyl hydroperoxide or tertiary amyl hydroperoxide to the cyclohexane fed to the oxidation reactor. These tertiary hydroperoxides have been found to be very effective for providing the free radicals which would otherwise be missing because there is no catalyst to decompose the cyclohexyl hydroperoxide to form free radicals. This peroxidation is referred to herein as "initiated" peroxidation since it is the addition of the tertiary hydroperoxide which "initiates" the reaction. These tertiary hydroperoxides are normally obtained by the known process of oxidizing the corresponding isoalkanes.

This oxidation of isoalkanes is carried out according to well known procedures to produce the maximum practical amount of the tertiary hydroperoxide compared to the tertiary alcohol produced. This results in 60 to 70% hydroperoxide and 30 to 40% alcohol since a higher ratio of hydroperoxide is not practical. The limitation on the maximum ratio of tertiary alcohol to tertiary hydroperoxide in the present invention is 1. The amount of tertiary hydroperoxide used in the invention is 0.5 to 5% so the maximum amount of tertiary alcohol is 5%. The minimum amount of tertiary alcohol used in U.S. Pat. No. 3,987,115 is 5% (mole ratio of alcohol to hydrocarbon of 0.05 to 1).

As previously indicated, the main products of the catalytic oxidation of cyclohexane are cyclohexanol and cyclohexanane with only a small amount of cyclohexyl hydroperoxide, perhaps 5 to 10% of the cyclohexane reacted. The process of the present invention involving initiated peroxidation rather than catalytic oxidation results in the formation of 60 to 80% cyclohexyl hydroperoxide with small amounts of the alcohol and ketone. The specific reaction rate and product distribution can be influenced to some extent by the amount of the tertiary hydroperoxide that is used for initiating the reaction.

The tertiary hydroperoxide initiated oxidation of a secondary carbon atom in cyclohexane results in the formation of cyclohexyl hydroperoxide at a rate comparable to the rate of the catalytic process but with a greatly reduced rate of decomposition of the cyclohexyl hydroperoxide. This is indicated by the small percentage of cyclohexanol and cyclohexanone in the product. This also shows that the free radical oxidation of cyclohexane is based on the thermal decomposition of the tertiary hydroperoxide rather than on the catalytic decomposition of the cyclohexyl hydroperoxide to provide the free radicals.

The peroxidation of the present invention is carried out by air or enriched air (oxygen concentration between 20% and 70%) at 100° C. to 200° C. and preferably 130° C. to 160° C. A reactor pressure is used which allows the removal of reaction heat by evaporation of the unreacted excess cyclohexane. This is typically 700 to 1200 kPa. The oxygen concentration in the vent gases, after condensation of the vapors, should be maintained at a relatively low level, preferably 1% to 5%, for reasons of operational safety and optimum reaction performance. The reaction mixture should be substantially free of dissolved metal ions, particularly transition metals, which would catalyze the decomposition of the cyclohexyl hydroperoxide. The reaction rate can be increased either by increasing the reaction temperature or by increasing the concentration of the tertiary hydroperoxide initiator. When 1% to 2% of the tertiary hydroperoxide is used, about 25% of it decomposes to form free radicals. This results in a conversion of 6% to 8% in the peroxidation of the cyclohexane.

The initiated peroxidation of the present invention is not limited to cyclohexane. The secondary carbon atoms in other cyclic and non-cyclic alkanes can also be oxidized to the corresponding hydroperoxide. For example, the direct oxidation of ethyl benzene is normally limited to 12% to 15% conversion. That is improved by use of the present invention to give a higher conversion and/or selectivity to produce ethyl-benzyl hydroperoxide. The preferred reaction temperature for the ethyl benzene would be approximately 110° C. to 115° C.

The following are examples of the process of the present invention:

EXAMPLE 1

Example 1 demonstrates the peroxidation of cyclohexane initiated by tertiary amyl hydroperoxide First, the tertiary amyl hydroperoxide was made by the non-catalytic oxidation of isopentane. In this oxidation, besides tertiary amyl hydroperoxide, some tertiary amyl alcohol, acetone and other by-products are also formed. The unreacted isopentane was distilled off and part of the remaining products of isopentane-oxidation was added to the peroxidation of cyclohexane.

The peroxidation of cyclohexane was carried out in a 4-liter stirred autoclave. After charging 1570 grams of cyclohexane into the autoclave, it was heated to 155° C. under nitrogen atmosphere. When the reaction temperature (155° C.) was reached a charge, consisting of:

35.1 g of tertiary amyl hydroperoxide
31.1 g of cyclohexane
2.8 g of tertiary amyl alcohol
8.1 g of isopentane and oxidation by-products was rapidly pumped into the autoclave and at the same time the addition of air, at a rate of 1.5 liters/min., was started. During the peroxidation, the reactor pressure was maintained at about 1000 kPa. by the continuous feeding of air. The concentration of oxygen in the vent gases, leaving the low temperature knock-back condenser, was about 5 vol. %. The condensate, mainly liquid cyclohexane, was returned continuously to the autoclave. Samples were withdrawn from the autoclave at 20, 40, 60 and 80 minutes. The samples were analyzed for cyclohexane, cyclohexyl hydroperoxide, cyclohexanol, cyclohexanone and by-products by a gas chromatograph. Also, titrations were used to determine the amount of total organic hydroperoxides and organic acids in the samples of the reaction mixture. The measured data for cyclohexane conversion and cyclohexyl/hydroperoxide selectivity have been plotted as functions of reaction time and are shown in FIG. 1.

The use of the initiator tertiary hydroperoxide produces a high conversion in a short time and the selectivity for the cyclohexyl hydroperoxide is enhanced versus the use of a tertiary alcohol.

The use of the tertiary hydroperoxide as initiator allows the non-catalytic peroxidation of cyclohexane to be carried out at lower temperatures and produces cyclohexyl hydroperoxide at high selectivity. Also, the achieved conversion of cyclohexane was higher than for the commercially used catalytic oxidations of cyclohexane.

The rate of oxidation is proportional to the reaction temperature and to the concentration of the initiator. To maintain a required reaction rate, these two independent variables have to be adjusted. The applicable temperature is limited by the desired selectivity of the secondary hydroperoxide while the cost of the initiator may limit its concentration in the reaction mixture.

Previous patents and literature in the 1960's, described a technique called co-oxidation, which can also be used to facilitate the oxidation of a slowly reacting hydrocarbon by the addition of a readily oxidizable compound. In the co-oxidation of isopentane and cyclohexane, both tertiary and secondary hydroperoxides are formed simultaneously which is not as effective as the proposed technique of initiated peroxidation of cyclohexane with tertiary amyl hydroperoxide.

The separate peroxidation of isopentane with the recovery of tertiary amyl hydroperoxide, followed by the initiated peroxidation of cyclohexane is more cost efficient than the co-oxidation process which has a slightly lower equipment cost. The co-oxidation is economically feasible only if a mixture of similar quantities of tertiary and secondary hydroperoxides is needed. In general, the products (alcohols/ketones) from the partial oxidation of the tertiary hydrocarbons are less valuable than the products from the secondary hydrocarbons. Therefore, economics would dictate the use of the minimum amount of initiator (tertiary hydroperoxide) required to achieve a commercially feasible production rate.

I claim:

1. A method for the peroxidation of secondary carbon in hydrocarbons selected from the group consisting of alkanes and cycloalkanes to produce hydroperoxides comprising contacting said hydrocarbon with molecular oxygen at a temperature of from 100° C. to 200° C. in the presence of a tertiary hydroperoxide initiator wherein said tertiary hydroperoxide initiator contains no more than 50 mole percent tertiary alcohol and the amount of tertiary hydroperoxide is from 0.5 to 5 mole percent of said hydrocarbon.

2. A method as claimed in claim 1 wherein said hydrocarbon is cyclohexane.

3. A method as claimed in claim 2 wherein said temperature is from 130° C. to 160° C.

4. A method as claimed in claim 3 wherein said peroxidation is at a pressure of 700 to 1200 kPa.

5. A method for the peroxidation of hydrocarbons selected from the group consisting of alkanes and cycloalkanes to produce hydroperoxides comprising the steps of contacting and reacting said hydrocarbon with oxygen at a temperature of 100° C. to 200° C. in the presence of an initiator consisting essentially of a tertiary hydroperoxide and wherein the amount of said tertiary hydroperoxide is from 0.5 to 5 mole percent of said hydrocarbon.

6. A method as claimed in claim 5 wherein said hydrocarbon is cyclohexane.

7. A method as claimed in claim 6 wherein said temperature is from 130° C. to 160° C.

8. A method as claimed in claim 7 wherein said reactions at a pressure of 700 to 1200 kPa.

9. A method as claimed in claim 5 wherein said tertiary hydroperoxide is selected from the group consisting of tertiary butyl hydroperoxide and tertiary amyl hydroperoxide.

10. A method for the peroxidation of cyclohexane to produce cyclohexyl hydroperoxide and to minimize the production of cyclohexanol and cyclohexanone comprising the steps of:

a. oxidizing an isoalkane and producing a product containing a tertiary hydroperoxide and a tertiary alcohol wherein said tertiary peroxide comprises at least 50 mole percent of said product, b. mixing said cyclohexane with said product to produce a mixture, said mixture containing from 1-5 mole percent of said tertiary hydroperoxide, and c. contacting said mixture with oxygen at a temperature of 100° C. to 200° C. to peroxidize said cyclohexane to cyclohexyl hydroperoxide.

* * * * *